United States Patent [19]

Sharifian et al.

[11] Patent Number: 5,389,211

[45] Date of Patent: Feb. 14, 1995

[54] METHOD FOR PRODUCING HIGH PURITY HYDROXIDES AND ALKOXIDES

[75] Inventors: Hossein Sharifian, Austin; David G. Diercks, Burleson, both of Tex.

[73] Assignee: Sachem, Inc., Austin, Tex.

[21] Appl. No.: 148,925

[22] Filed: Nov. 8, 1993

[51] Int. Cl.[6] .............................................. C25B 3/00
[52] U.S. Cl. ..................................... 204/72; 204/131
[58] Field of Search ................ 204/59 R, 72, 130, 131

[56] References Cited

U.S. PATENT DOCUMENTS

| | | | |
|---|---|---|---|
| 4,394,226 | 7/1983 | Wade et al. | 204/72 |
| 4,425,202 | 1/1984 | Sullivan | 204/72 |
| 4,521,285 | 6/1985 | DeWitt et al. | 204/72 |
| 4,572,769 | 2/1986 | Shimizu | 204/59 R |
| 4,714,530 | 12/1987 | Hale et al. | 204/131 |
| 4,938,854 | 7/1990 | Sharifian | 204/130 |

FOREIGN PATENT DOCUMENTS

| | | |
|---|---|---|
| 60-131985 | 7/1985 | Japan . |
| 131986 | 7/1985 | Japan . |
| 60-131986 | 7/1985 | Japan . |
| 2129390 | 5/1990 | Japan . |

*Primary Examiner*—John Niebling
*Assistant Examiner*—Edna Wong
*Attorney, Agent, or Firm*—Renner, Otto, Boisselle & Sklar

[57] ABSTRACT

Processes are described for preparing organic and inorganic hydroxides or alkoxides and for improving the purity of organic and inorganic hydroxides or alkoxides utilizing an electrolysis cell. For example, a process for improving the purity of an organic or inorganic hydroxide is described, and the process comprises the steps of:

(A) providing an electrolysis cell which comprises an anolyte compartment containing an anode, a catholyte compartment containing a cathode and water, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising the organic or inorganic hydroxide and an oxidizable liquid to the anolyte compartment;

(C) passing a current through the electrolysis cell to produce a purified organic or inorganic hydroxide in the catholyte compartment; and (D) recovering the purified organic or inorganic hydroxide from the catholyte compartment.

The process of the invention is effective in lowering the content of anions such as halide, nitrite, nitrate, carbonate, etc., some cations such as zinc, calcium, etc., and neutral organic materials such as methanol, amines, etc.

39 Claims, 1 Drawing Sheet

METHOD FOR PRODUCING HIGH PURITY HYDROXIDES AND ALKOXIDES

TECHNICAL FIELD

This invention relates to a method of preparing organic and inorganic hydroxides or alkoxides and for improving the purity of organic and inorganic hydroxides or alkoxides. More particularly, the invention relates to a method of improving the purity of quaternary ammonium hydroxides. The invention also relates to the high purity hydroxides and alkoxides obtained by the method of the invention.

BACKGROUND OF THE INVENTION

Quaternary ammonium hydroxides such as tetramethylammonium hydroxide (TMAH) and tetraethyl ammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium, potassium, zinc and calcium; anions such as halides, nitrates, nitrites, carbonates, carboxylates, sulfates and neutral organic species such as methanol, amines, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium compound in an electrolysis cell containing a diaphragm formed of a cation-exchange membrane. The quaternary ammonium salts used in such preparations include halide salts, carboxylate salts, carbonate salts and sulfate salts. When halide salts are used in the manufacture of quaternary ammonium hydroxide, it has been discovered that the quaternary ammonium hydroxide solutions formed by this method generally contain significant amounts of halogen (ionic and latent), generally in concentrations from about 30 ppm up to about 100 ppm at 25% quaternary ammonium hydroxide (e.g., TMAH). The term "latent halide" is used throughout this specification and claims to refer to non-ionic halogen which is present in the aqueous quaternary ammonium hydroxide solutions, and which is capable of forming halide ions under certain conditions such as heating.

Among the prior art patents which describe the preparation of quaternary ammonium hydroxides by electrolyzing a salt of a quaternary ammonium compound are U.S. Pat. Nos. 4,572,769 (Shimizu); 4,521,285 (DeWitt et at); 4,425,202 (Sullivan); and 4,394,226 (Wade et at). U.S. Pat. No. 4,572,769 describes the use of formate salts to form the quaternary ammonium hydroxides, and this patent suggests that some of the problems of using quaternary ammonium halides are minimized by use of the formate salt. The formate salts are prepared by the reaction of a trialkyl amine with methyl formate in either methanol or ethanol as solvent. U.S. Pat. No. 4,521,285 describes an electrolytic process for removing the anion from quaternary organic salts. The process uses a cell comprising four compartments containing two cation exchange membranes and one anion exchange membrane. U.S. Pat. No. 4,425,202 describes a process for making choline base by electrolysis of choline chloride in an electrolytic cell. Color stabilization of choline base is effected through concentration control and/or the addition of a sulfite prior to electrolytic manufacture of the choline base. U.S. Pat. No. 4,394,226 describes production of quaternary ammonium hydroxides in electrolytic cells using cationic membranes which have been treated with a mineral acid prior to use in the electrolysis.

U.S. Pat. No. 4,714,530 (Hale et al) describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

U.S. Pat. No. 4,938,854 (Sharifian et at) also describes an electrolytic process for purifying quaternary ammonium hydroxides by lowering the latent halide content. The electrolytic cell may be divided into an anolyte compartment and a catholyte compartment by a divider which may be an anion or cation selective membrane. The cathode in the catholyte compartment comprises zinc, cadmium, tin, lead, copper or titanium, or alloys thereof, mercury or mercury amalgam.

Japanese Kokai Patent No. 60-131985 (1985) (Takahashi et al) describes a method of manufacturing a high purity quaternary ammonium hydroxide in an electrolysis cell which is divided into an anode chamber and a cathode chamber by a cation exchange membrane. A quaternary ammonium hydroxide solution containing impurities is charged to the anode chamber and a direct current is supplied between two electrodes after water has been charged to the cathode chamber. Purified quaternary ammonium hydroxide is obtained from the cathode chamber. The purified quaternary ammonium hydroxide contains reduced amounts of alkali metals, alkaline earth metals, anions, etc.

Japanese Kokai Patent No. 60-131986 (1985) (Takahashi et at) describes a method for manufacturing a high purity quaternary ammonium hydroxide. The method described in this patent utilizes an electrolysis cell which has been compartmentalized into an anode chamber, a cathode chamber, and at least one intermediate chamber with at least two cation exchange membranes. An aqueous solution containing a quaternary ammonium salt is charged to the anode chamber, water is charged to the cathode chamber, and an aqueous hydroxide solution corresponding to the quaternary ammonium salt charged into the anode chamber is charged into the intermediate chamber. Upon application of a direct current, a quaternary ammonium hydroxide is formed in the cathode chamber and recovered.

SUMMARY OF THE INVENTION

Processes are described for preparing organic and inorganic hydroxides or alkoxides and for improving the purity of organic and inorganic hydroxides or alkoxides utilizing an electrolysis cell. For example, a process for improving the purity of an organic or inorganic hydroxide is described, and the process comprises the steps of:

(A) providing an electrolysis cell which comprises an anolyte compartment containing an anode, a catholyte compartment containing a cathode and water, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising the organic or inorganic hydroxide and an oxidizable liquid to the anolyte compartment;

(C) passing a current through the electrolysis cell to produce a purified organic or inorganic hydroxide in the catholyte compartment; and (D) recovering the purified organic or inorganic hydroxide from the catholyte compartment.

The processes of the invention are effective in lowering the content of anions such as halide, nitrite, nitrate, carbonate, sulfate, carboxylate (e.g., formate), etc., some cations such as sodium, potassium, zinc, calcium, etc., and neutral organic materials such as methanol, amines, etc.

DESCRIPTION OF THE PREFERRED EMBODIMENTS

Figure 1:
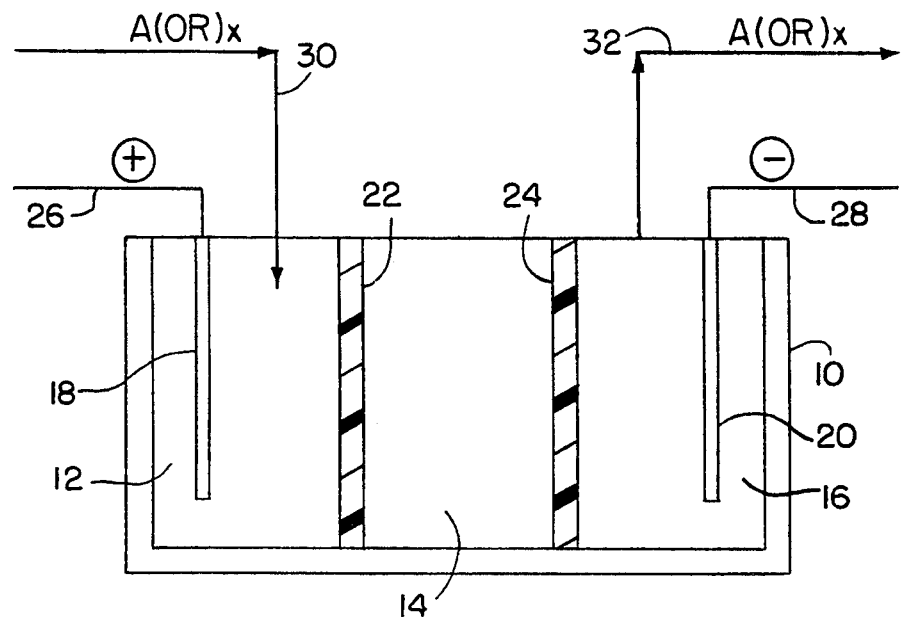
FIG. 1 is a schematic cross-section of an electrolytic cell useful in performing the process of the invention.

In one embodiment, the process of the present invention is useful in purifying organic and inorganic hydroxides or alkoxides. The process for purifying organic and inorganic hydroxides comprises the steps of (A) providing an electrolysis cell which comprises an anolyte compartment containing an anode, a catholyte compartment containing a cathode and water, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising the organic or inorganic hydroxide and an oxidizable liquid to the anolyte compartment;

(C) passing a current through the electrolysis cell to produce a purified organic or inorganic hydroxide in the catholyte compartment; and (D) recovering the purified organic or inorganic hydroxide from the catholyte compartment.

The process for purifying organic and inorganic alkoxides comprises the steps of (A) providing an electrolysis cell which comprises an anolyte compartment containing an anode, a catholyte compartment containing a cathode and an alcohol corresponding to the alkoxide, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising the organic or inorganic alkoxide and an oxidizable liquid to the anolyte compartment;

(C) passing a current through the electrolysis cell to produce a purified organic or inorganic alkoxide in the catholyte compartment; and (D) recovering the purified organic or inorganic alkoxide from the catholyte compartment.

The hydroxides and alkoxides may generally be characterized by the formula $$A(OR)_x \qquad (I)$$

wherein A is an organic or inorganic group, R is hydrogen or an alkyl group, and x is an integer equal to the valence of A. In one embodiment, the hydroxides and alkoxides should be sufficiently soluble in the water, alcohol or organic liquid, or mixtures thereof to allow a useful conversion rate.

Examples of inorganic hydroxides and alkoxides which can be purified in accordance with the present invention, include the hydroxides and alkoxides of alkali metals such as sodium and potassium; alkaline earth metals such as magnesium and calcium; transition metals such as titanium, zirconium, chromium, manganese, iron, cobalt, nickel, copper, platinum; rare earth metals such as cerium, neodymium, samarium; etc. Specific examples of inorganic hydroxides and alkoxides which can be purified in accordance with the process of the present invention include potassium hydroxide, potassium methoxide, potassium ethoxide, magnesium hydroxide, ferrous hydroxide, ferric hydroxide, cuprous hydroxide, cupric hydroxide, cobaltous hydroxide, cobaltic hydroxide, etc.

In another embodiment the process of the present invention is useful in preparing purified organic hydroxides and alkoxides such as quaternary ammonium hydroxides and alkoxides, quaternary phosphonium hydroxides and tertiary sulfonium hydroxides.

The quaternary ammonium and quaternary phosphonium hydroxides and alkoxides may be characterized by the formula

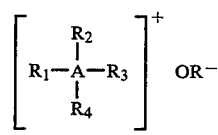

(II)

wherein A is a nitrogen or phosphorus atom, R is hydrogen or an alkyl group, $R_1$, $R_2$, $R_3$ and $R_4$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with A may form a heterocyclic group provided that if the heterocyclic group contains a C=A group, $R_3$ is the second bond.

The alkyl group R generally is a lower alkyl group containing from 1 to 4 carbon atoms. Methyl and ethyl groups are preferred. The alkyl groups $R_1$ to $R_4$ may be linear or branched, and specific examples of alkyl groups containing from 1 to 20 carbon atoms include methyl, ethyl, propyl, butyl, pentyl, hexyl, heptyl, octyl, isooctyl, nonyl, octyl, decyl, isodecyl, dodecyl, tridecyl, isotridecyl, hexadecyl and octadecyl groups. $R_1$, $R_2$, $R_3$ and $R_4$ also may be hydroxyalkyl groups such as hydroxyethyl and the various isomers of hydroxypropyl, hydroxybutyl, hydroxypentyl, etc. In one preferred embodiment, $R_1$–$R_4$ are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, and equivalent groups wherein benzene rings have been substituted with one or more hydroxy groups.

The quaternary ammonium hydroxides and alkoxides which can be purified in accordance with the process of the present invention may be represented by Formula III

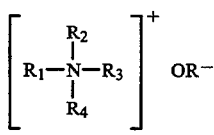

wherein R and $R_1$–$R_4$ are as defined in Formula II. In one preferred embodiment, $R_1$–$R_4$ are alkyl groups containing from 1 to about 3 carbon atoms and hydroxyalkyl groups containing 2 or 3 carbon atoms. Most often the quaternary ammonium hydroxides purified in accordance with the process of the invention will be tetramethylammonium hydroxide (TMAH) or tetraethylammonium hydroxide (TEAH). Specific examples of other such hydroxides and alkoxides include tetramethylammonium hydroxide, tetramethylammonium hydroxide, tetraethylammonium hydroxide, tetraethylammonium hydroxide, tetrapropylammonium hydroxide, tetrabutylammonium hydroxide, tetra-n-octylammonium hydroxide, trimethylhydroxyethylammonium hydroxide, trimethylmethoxyethylammonium hydroxide, dimethyldihydroxyethylammonium hydroxide, methyltrihydroxyethylammonium hydroxide, phenyltrimethylammoniumhydroxide, phenyltriethylammoniumhydroxide, benzyltrimethylammonium hydroxide, benzyltriethylammonium hydroxide, dimethylpyrolidinium hydroxide, dimethylpiperidinium hydroxide, diisopropylimidazolinium hydroxide, N-alkylpyridinium hydroxide, etc., and the corresponding alkoxides such as the corresponding methoxides and ethoxides.

Examples of quaternary phosphonium hydroxides and alkoxides representative of Formula II wherein A=P which can be purified in accordance with the process of the present invention include tetramethylphosphonium hydroxide, tetraethylphosphonium hydroxide, tetrapropylphosphonium hydroxide, tetrabutylphosphonium hydroxide, trimethylhydroxyethylphosphonium hydroxide, dimethyldihydroxyethylphosphonium hydroxide, methyltrihydroxyethylphosphonium hydroxide, phenyltrimethylphosphonium hydroxide, phenyltriethylphosphonium hydroxide and benzyltrimethylphosphonium hydroxide, and the corresponding methoxides and ethoxides.

In another embodiment, the tertiary sulfonium hydroxides and alkoxides which can be purified in accordance with this invention may be represented by the formula

wherein R is hydrogen or a lower alkyl group of 1 to about 4 carbon atoms, and $R_1$, $R_2$ and $R_3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with S may form a heterocyclic group provided that if the heterocyclic group contains a C=S group, $R_3$ is the second bond.

Examples of the hydroxides and alkoxides represented by Formula IV include trimethylsulfonium hydroxide, trimethylsulfonium hydroxide, triethylsulfonium hydroxide, tripropylsulfonium hydroxide, etc., and the corresponding methoxides and ethoxides.

The hydroxides which are purified in accordance with the process of the present invention are mixtures, preferably solutions, containing an oxidizable liquid and from about 3% to about 55% by weight of the hydroxide and generally will contain varying amounts of one or more undesirable anions such as halide, carbonate, formate, nitrite, nitrate, etc., some cations such as metals including zinc and calcium, and some neutral species such as methanol, amines, etc. For example, aqueous solutions of quaternary ammonium hydroxides prepared by the electrolysis of quaternary ammonium halides typically may contain, at 25% by weight of quaternary ammonium hydroxide, from about 15 to about 500 ppm of ionic halide, from about 5 to about 75 ppm of latent halide and up to about 10,000 ppm of nitrate. Unless otherwise specifically indicated in this application all references to ppm of halide, metals, or carbonates, etc., are for aqueous solutions containing 25% by weight of the quaternary ammonium hydroxide.

In one embodiment, the process of the present invention is effective in reducing the amount of nitrate and ionic halide present in quaternary ammonium hydroxides. In a further embodiment, the process of the present invention results in a reduction of both latent and ionic halide as well as nitrate in a quaternary ammonium hydroxide.

As noted above, when the process is used to purify a hydroxide, the catholyte compartment of the electrolysis cell provided in step (A) contains water, and the intermediate compartment(s) contains water, an organic liquid or mixture of water and an organic liquid. These compartments also may contain organic or inorganic hydroxide prior to initiation of the electrolysis. For example, the solution in the catholyte compartment and/or the intermediate compartments of the electrolysis cell may contain from about 4% to about 60% by weight or more of the hydroxide. The catholyte compartment and intermediate compartment also may include one or more organic liquids. Examples of such organic liquids include hydrocarbons, alcohols, ethers, etc., or mixtures thereof. However, during electrolysis, liquid in the catholyte compartment should comprise sufficient water to form the desired hydroxide. More specific examples of organic liquids which may be used include methanol, ethanol, propanol, ethylene glycol, diethylene glycol, hexane, heptane, benzene, toluene, xylene, etc. The mixture charged to the catholyte or intermediate compartments preferably should not contain significant amounts of any liquid which can react with a hydroxyl group. Examples of such organic liquids which should be avoided in the catholyte mixture include acids, esters, ketones, aldehydes, amides, etc. It is also preferred to avoid any liquid in the catholyte mixture in which the desired hydroxide or alkoxide product is insoluble.

When the process of the present invention is utilized to improve the purity of an organic or inorganic hydroxide, a mixture is charged to the anolyte compartment which comprises the organic or inorganic hydroxide and an oxidizable liquid. Any oxidizable liquid which can react at the anode is useful in the process of the invention. Examples of such oxidizable liquids include water, alcohols such as methanol, ethanol, propanol, ethylene glycol and diethylene glycol, hydrocarbons such as hexane, heptane, benzene, toluene, xylene, etc. Mixtures of such liquids may be utilized. Water, alcohols, or mixtures of water and alcohols are preferred. Concentration of the organic or inorganic alkoxide in the catholyte mixture generally will be in the range of from about 3% to about 55% by weight.

When the process of the present invention is utilized to purify an organic or inorganic alkoxide, the catholyte compartment of the electrolysis cell provided in step (A) contains alcohol, and the intermediate compartment(s) may contain water, or a mixture of water and an organic liquid. The alcohol in the catholyte compartment is an alcohol corresponding to the alkoxide to be purified. For example, if the alkoxide being purified is a methoxide, the alcohol in the catholyte compartment is methanol; if the alkoxide is an ethoxide, the alcohol is ethanol; etc. The catholyte and intermediate compartments also may contain organic or inorganic alkoxide prior to the initiation of the hydrolysis. The organic liquids which may be utilized in the intermediate compartments include hydrocarbons, alcohols, ethers, etc., or mixtures thereof. Specific examples of such organic liquids include methanol, ethanol, propanol, ethylene glycol, diethylene glycol, hexane, heptane, benzene, toluene, xylene, etc. Generally, it is desired to avoid any liquid in the catholyte mixture in which the desired alkoxide product is insoluble.

When the process of the present invention is utilized to improve the purity of organic and inorganic alkoxides, the mixture charged to the anolyte compartment of the electrolysis cell in step (B) comprises the organic or inorganic alkoxide and an oxidizable liquid. Any of the oxidizable liquids described above can be utilized, and the preferred oxidizable liquids are alcohols such as methanol, ethanol or propanol, water, or mixtures of water and alcohol. The concentration of the organic or inorganic alkoxide in the oxidizable liquid in the anolyte compartment may range from about 3% to about 55% by weight.

The process of the present invention also is useful for preparing organic or inorganic hydroxides from the corresponding alkoxides, and the process is particularly useful for preparing such alkoxides from hydroxides containing various undesirable anions such as halide, carbonate, formate, nitrate, nitrite, etc., cations such as metals including zinc and calcium, and some neutral species such as methanol, amines, etc. More particularly, organic and inorganic hydroxides can be prepared from the corresponding alkoxides by the process which comprises the steps of (A) providing an electrolysis cell which comprises an anolyte compartment containing an anode, a catholyte compartment containing a cathode and water, and at least one intermediate compartment containing water, an organic liquid or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising an oxidizable liquid and the organic or inorganic alkoxide to the anolyte compartment;

(C) passing a current through the electrolysis cell to produce an organic or inorganic hydroxide in the catholyte compartment; and (D) recovering the purified organic or inorganic hydroxide and water from the catholyte compartment.

The organic and inorganic hydroxides which can be prepared from the corresponding alkoxide may be any of the hydroxides described earlier by Formula I $$A(OR)_x \qquad (I)$$

wherein R is hydrogen and A and x are as defined previously. As noted, the organic or inorganic alkoxide is charged to the anolyte compartment, and the desired corresponding hydroxide is recovered from the catholyte compartment. The mixture charged to the anolyte compartment comprises an oxidizable liquid and the organic or inorganic alkoxide. Any of the oxidizable liquids described above can be utilized, and generally, the oxidizable liquid will be an alcohol or water.

Since the desired product is the organic or inorganic hydroxide, the catholyte compartment contains water or a mixture of water and an organic solvent provided that the catholyte compartment contains sufficient water to form the desired organic or inorganic hydroxide. The intermediate compartment(s) may contain water, an organic liquid as described above, or a mixture of water and an organic liquid.

In one preferred embodiment, the process of the invention is utilized in preparing organic hydroxides from the corresponding alkoxides, and preferred examples of organic hydroxides include the quaternary ammonium hydroxides, phosphonium hydroxides and tertiary sulfonium hydroxides described above and represented by Formulae II, III and IV. The concentration of the alkoxide in the mixture contained in the anolyte compartment may range from about 3% to about 55% by weight.

The process of the present invention also may be utilized for preparing organic and inorganic alkoxides from the corresponding hydroxides. This process comprises the steps of (A) providing an electrolysis cell which comprises an anolyte compartment containing an anode, a catholyte compartment containing a cathode and an alcohol corresponding to the alkoxide, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;

(B) charging a mixture comprising the organic or inorganic hydroxide and an oxidizable liquid to the anolyte compartment;

(C) passing a current through the electrolysis cell to produce a purified organic or inorganic alkoxide in the catholyte compartment; and (D) recovering the organic or inorganic alkoxide from the catholyte compartment.

As noted, the mixture charged to the anolyte compartment in step (B) comprises a mixture of the organic or inorganic hydroxide and an oxidizable liquid. Any of the oxidizable liquids described above including water and alcohols may be utilized. The concentration of the organic or inorganic hydroxide in the mixture may range from about 3% to about 55% by weight. When the desired product is an organic or inorganic alkoxide, the catholyte compartment contains an alcohol which corresponds to the desired alkoxide, and more particularly, an alcohol which will form the desired alkoxide. If the desired alkoxide is a methoxide, the alcohol in the catholyte compartment is methanol. If the desired alkoxide is an ethoxide, then the alcohol in the catholyte compartment is ethanol. The intermediate compartment may contain water, an organic liquid or a mixture of water and an organic liquid. The organic liquid may be an alcohol and more particularly the alcohol corresponding to the desired alkoxide. Any of the organic liquids described above may be utilized in the intermediate compartment of this embodiment. In a preferred embodiment, the hydroxide charged in step (B) is an organic hydroxide and more often will be a quaternary ammonium hydroxide, a phosphonium hydroxide or a tertiary sulfonium hydroxide such as described above and represented by Formulae II, III and IV.

The electrolysis cell utilized in the processes of the present invention comprises at least three compartments: an anolyte compartment containing an anode, a catholyte compartment containing a cathode and at least one intermediate compartment. The catholyte compartment is separated from the intermediate compartment(s) by a nonionic divider or a cation selected membrane, and the anolyte compartment is separated from the intermediate compartment(s) by a second divider or cation selective membrane. The type of electrolysis cell used in the processes of the present invention may be any of the known electrolysis cells, and the cells may be composed of conventional cell materials which are compatible with the materials being charged into or formed in the compartments of the cells.

Various materials which have been used as anodes in electrolysis cells can be included in the cells used in the above and other embodiments of the present invention provided they do not react with the solution added to the cells. For example, the anode may be made of high purity graphite or metals such as, for example, titanium-coated or clad electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

Various materials which have been used as cathodes in electrolytic cells can be included in the cells used in the above and other embodiments of the present invention. Cathode materials include nickel, iron, stainless steel, nickel plated titanium, etc. Preferably, the cathodes in electrolytic cells utilized in the process of the present invention comprise zinc, cadmium, nickel, tin, lead, copper, iron or titanium or alloys thereof, mercury or mercury amalgams. The term "alloy" is used in a broad sense and includes intimate mixtures of two or more metals as well as one metal coated onto another metal. The mercury amalgam cathodes include, for example, mercury on nickel, mercury on copper, mercury on cadmium, mercury on zinc, etc.

The electrolysis cell utilized in the process of the present invention contains at least two dividers which may be nonionic dividers or selective membranes. One divider separates the anolyte compartment from the intermediate compartment(s), and a second divider separates the catholyte compartment from the intermediate compartment(s). Thus, the intermediate compartment(s) is (are) defined as the area between these two dividers. The dividers function as diffusion barriers and gas separators. Examples of nonionic divider materials include fabrics, sintered glass, glass frits, ceramics, membrane diaphragms, etc.

The cation selective membranes may be any of those which have been used in the electrolysis of quaternary ammonium salts to quaternary ammonium hydroxides. Preferably, the cation-exchange membranes should comprise a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic acid/perfluorocarboxylic acid, perfluorocarbon polymer membranes such as sold by the E.I. dupont Nemours & Co. under the general trade designation "Nation." Other suitable cation selective membranes include styrenedivinyl benzene copolymer membranes containing cation selective groups such as sulfonate groups, carboxylate groups, etc. The preparation and structure of cation selective membranes are described in the chapter entitled "Membrane Technology" in *Encyclopedia Of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

A schematic cross-section or representation of a three compartment electrolysis cell useful in the processes of the present invention described above is shown in FIG. 1. In FIG. 1, the electrolytic cell 10 comprises an anolyte compartment 12, a catholyte compartment 16 and an intermediate compartment 14. The anolyte compartment 12 is separated from the intermediate compartment 14 by a divider 22, and the catholyte compartment 16 is separated from the intermediate compartment 14 by divider 24. The anolyte compartment contains an anode 18 which is attached to the power supply (not shown) by wire 26. The catholyte compartment 16 contains a cathode 20 attached to a power supply (not shown) through wire 28. With reference to FIG. 1, the anolyte mixture containing a hydroxide or alkoxide (A(OR)D is charged to the anolyte compartment as illustrated by line 30, and the catholyte comprising a purified aqueous solution of hydroxide or alkoxide after electrolysis is recovered from the catholyte compartment as shown by line 32. Although not shown in FIG. 1, the intermediate compartment 14 may be further sub-divided into additional compartments by dividing the intermediate compartment 14 with additional dividers. The use of additional dividers increases the cost of the electrolysis cell and the consumption of electricity, but the inclusion of additional dividers generally will result in an increase in the purity of the hydroxide or alkoxide recovered from the catholyte compartment.

The concentration of hydroxide or alkoxide in the mixture charged to the anolyte compartment of an electrolysis cell in accordance with the above processes generally will be from about 3% to about 55% by weight. More generally, the concentration will be from about 5% to about 30% by weight. The concentration of hydroxide or alkoxide in the catholyte compartment preferably is higher than the concentration in the anolyte compartment. Generally, the catholyte mixture will contain from 5% to about 60% by weight of the desired hydroxide or alkoxide. The intermediate compartment(s) may also contain the organic or inorganic hydroxide. Mixtures in the intermediate compartment may contain from about 4% to about 60% of the hydroxide or alkoxide. In order to maximize membrane life, it is preferred that the concentration of hydroxide or alkoxide increases from the anode compartment to the intermediate compartment to the catholyte compartment. During the electrolysis, it is desirable that the temperature of the liquid within the cell be maintained within the range of from about 10° C. to about 70° C., and more generally, the temperature is maintained at about 50°-60° C. during electrolysis.

Electrolysis of the mixture containing the organic or inorganic hydroxide or alkoxide contained in the anolyte compartment is effected by impressing a current voltage (generally direct current) between the anode and the cathode with a current density of about 5 to about 250 A/ft$^2$, and more preferably at a current density of from about 25 to about 150 A/ft$^2$. Alternatively, the current density may be about 1–100 A/dm$^2$ or 10–50 A/dm$^2$. The current density is applied to the cell for a period of time which is sufficient to result in the formation of the desired amount of the hydroxide or alkoxide in the catholyte. Circulation is effected by pumping and/or by gas evolution. In practice, such electrolysis cell can be operated batchwise or in a continuous operation.

In one embodiment, the aqueous mixture containing a quaternary ammonium hydroxide which is to be charged into the anolyte compartment in step (B) is heated to an elevated temperature for an extended period of time prior to treatment in electrolysis cell. The purity of the quaternary ammonium hydroxide recovered from the subsequent electrolysis step is improved when the original quaternary ammonium hydroxide solution which is to be charged to the anolyte compartment of the electrolysis cell is first heated to a temperature of from about 50° C. to about 200° C., and more preferably at a temperature of from about 80° C. to about 175° C. The heating generally is conducted for a period of from about 0.1 hour to about 4 days or more, and more generally for a period of from about 0.2 hour, up to about one day. The length of time of the heating can be reduced by raising the temperature. However, the temperature should not be so high as to result in the decomposition of significant amounts of the desired product. The heated quaternary ammonium hydroxide solution can be cooled prior to being charged to the anolyte compartment of the electrolysis cell, but cooling is not required. Although it is not understood completely why this preheating step improves the purity of the formed quaternary ammonium hydroxide recovered from the catholyte compartment, such pretreatment results in the recovery of quaternary ammonium hydroxides containing lesser amounts of halide impurities. It has been observed that this heating step per se does not reduce the ionic halide content of the heated material, and more often the heating step increases the ionic halide content. The latent halide content is, however, significantly reduced by the heating procedure. Typical properties of a 25% aqueous solution of quaternary hydroxide purified and recovered from the preferred process of this invention (preheating step included) are: 0–10 ppm of ionic halide; 0–5 ppm of latent chloride; 0–200 ppm of carbonate; less than 100 ppb of nitrate; 0–50 ppb heavy metals; and a colorless solution.

Figure 2:
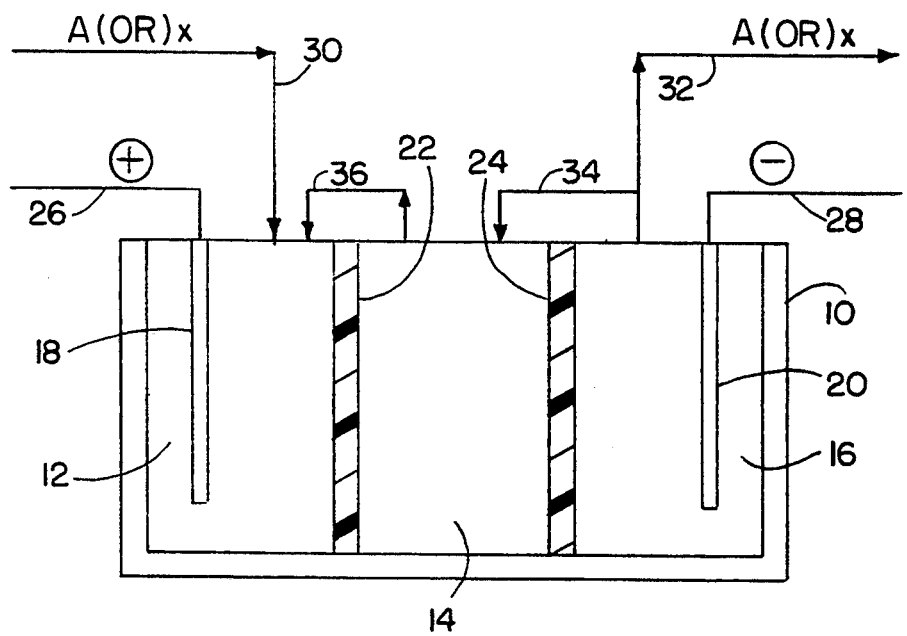
FIG. 2 is a schematic cross-section of a preferred electrolytic cell useful in performing the process of the invention.

Another embodiment of the invention is illustrated in FIG. 2. This embodiment is useful particularly for purifying hydroxides and alkoxides as described above. The cell depicted in FIG. 2 is essentially the same as the cell of FIG. 1 except that a portion of the hydroxide or alkoxide mixture recovered from the catholyte compartment 16 as shown by arrow 32 is charged to the intermediate compartment 14 as shown by arrow 34. The purified hydroxide or alkoxide recovered from catholyte compartment 16 may be charged to the intermediate compartment intermittently or in a continuous manner. A portion of the solution in the intermediate compartment 14 may be removed and charged to the anolyte compartment as shown by line 36 in FIG. 2, or a portion of the solution in intermediate compartment 14 may be removed and forwarded to an internal holding tank (not shown) or discarded. The amount of solution removed from intermediate compartment 14 generally will be an amount substantially equivalent to the amount of hydroxide or alkoxide mixture removed from the catholyte compartment and charged to the intermediate compartment as shown by line 34 thereby maintaining the level of the solution in the intermediate compartment. The purpose for charging purified hydroxide or alkoxide to the intermediate compartment while removing a portion of the solution in the intermediate compartment is to avoid the build-up of impurities in the intermediate compartment. The amount of the purified hydroxide or alkoxide charged to the intermediate compartment 14 may vary as desired, and generally about 1% to about 10%, preferably about 5% of the total catholyte compartment output is recirculated to the intermediate compartment 14.

The following examples illustrate the processes of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

A three-compartment electrolysis cell is prepared equipped with a titanium anode coated with ruthenium oxide, a nickel cathode and two cation selective membranes (Nation 902 from DuPont). The two membranes are separated by means of a 0.5-inch thick polypropylene divider. Deionized water containing 1% by weight of pure tetramethylammonium hydroxide is added to the intermediate compartment and to the catholyte compartment. A one-molar aqueous tetramethylammonium hydroxide solution containing 500 ppm of ionic chloride and 6000 ppm nitrate is charged to the anolyte compartment, and the intermediate compartment is constantly purged with the solution recovered from the catholyte compartment after electrolysis to avoid impurity build-up. In this example, the flow of tetramethylammonium hydroxide solution from the catholyte compartment into the intermediate compartment is adjusted at a rate of 5% of the total output of the catholyte. The electrolysis is carded out at a current density of 1.0 A/inch$^2$ at a temperature of 55° C. until a 1.45M solution of tetramethylammonium hydroxide is obtained in the catholyte compartment. Analysis of the solutions in the intermediate and catholyte compartments on a basis of 25% tetramethylammonium hydroxide indicates an ionic chloride content of 0.75 ppm and 0.25 ppm, respectively, a nitrate content of 5 ppm and less than 0.1 ppm, respectively; and a methanol content of 100 ppm and less than 10 ppm, respectively.

EXAMPLE 2

The general procedure of Example 1 is repeated except that the intermediate compartment is equipped with a dedicated internal tank. Purified tetramethylammonium hydroxide solution is constantly circulated from the catholyte compartment into the intermediate compartment and the internal tank. The analysis of the tetramethylammonium hydroxide solution in the catholyte compartment at 25% tetramethylammonium hydroxide shows 0.20 ppm of ionic chloride, less than 0.1 ppm of nitrate and less than 10 ppm of methanol.

EXAMPLE 3

The general procedure of Example 1 is repeated except that a one-molar aqueous tetraethylammonium hydroxide solution containing 700 ppm of ionic chloride is charged to the anolyte compartment. The electrolysis is carried out at a current density of 0.5 A/inch$^2$ at a temperature of 45° C. until a 1.42M solution of tetraethylammonium hydroxide is obtained in the catholyte compartment. Analysis of the solutions in the intermediate and catholyte compartments on a basis of 20% tetraethylammonium hydroxide indicate chloride content of about 10 ppm and about 1 ppm, respectively.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for improving the purity of an organic or inorganic hydroxide which comprises the steps of
   (A) providing an electrolysis cell which comprises an anolyte compartment containing an anode, a catholyte compartment containing a cathode and water, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;
   (B) charging a mixture comprising the organic or inorganic hydroxide and an oxidizable liquid to the anolyte compartment;
   (C) passing a current through the electrolysis cell to produce a purified organic or inorganic hydroxide in the catholyte compartment; and
   (D) recovering the purified organic or inorganic hydroxide from the catholyte compartment.

2. The process of claim 1 wherein the dividers are cation selective membranes.

3. The process of claim 1 wherein the hydroxide charged to the anolyte compartment in step (B) is an organic hydroxide.

4. A process for improving the purity of an organic or inorganic alkoxide which comprises the steps of
   (A) providing an electrolysis cell which comprises an anolyte compartment containing an anode, a catholyte compartment containing a cathode and an alcohol corresponding to the alkoxide, and at least one intermediate compartment containing water, an organic liquid, or a mixture of water and an organic, said at least one intermediate compartment being separated from the anolyte and catholyte compartments by at least two dividers selected from nonionic dividers, cation selective membranes, or combinations thereof;
   (B) charging a mixture comprising the organic or inorganic alkoxide and an oxidizable liquid to the anolyte compartment;
   (C) passing a current through the electrolysis cell to produce a purified organic or inorganic alkoxide in the catholyte compartment; and
   (D) recovering the purified organic or inorganic alkoxide from the catholyte compartment.

5. The process of claim 4 wherein the dividers are cation selective membranes.

6. The process of claim 4 wherein the alkoxide charged to the anolyte compartment in step (B) is an organic alkoxide.

7. The process of claim 4 wherein the alkoxide charged in step (B) is a quaternary ammonium alkoxide, a phosphonium alkoxide, or a tertiary sulfonium alkoxide.

8. A process for preparing an organic or inorganic hydroxide from the corresponding alkoxide which comprises the steps of
   (A) providing an electrolysis cell which comprises an anolyte compartment containing an anode, a catholyte compartment containing a cathode and water, and at least one intermediate compartment containing water, an organic liquid or a mixture of water and an organic liquid, said at least one intermediate compartment being separated from the anolyte and catholyte compartments by at least two dividers selected from nonionic dividers, cation selective membranes, or combinations thereof;
   (B) charging a mixture comprising an oxidizable liquid and the organic or inorganic alkoxide to the anolyte compartment;
   (C) passing a current through the electrolysis cell to produce an organic or inorganic hydroxide in the catholyte compartment; and
   (D) recovering the purified organic or inorganic hydroxide and water from the catholyte compartment.

9. The process of claim 8 wherein the dividers are cation selective membranes.

10. The process of claim 8 wherein the alkoxide charged to the anolyte compartment in step (B) is an organic alkoxide.

11. The process of claim 8 wherein the alkoxide charged in step (B) is a quaternary ammonium alkoxide, a phosphonium alkoxide, or a tertiary sulfonium alkoxide.

12. A process for preparing an organic or inorganic alkoxide from the corresponding hydroxide which comprises the steps of
   (A) providing an electrolysis cell which comprises an anolyte compartment containing an anode, a catholyte compartment containing a cathode and an alcohol corresponding to the alkoxide, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;
   (B) charging a mixture comprising the organic or inorganic hydroxide and an oxidizable liquid to the anolyte compartment;
   (C) passing a current through the electrolysis cell to produce a purified organic or inorganic alkoxide in the catholyte compartment; and
   (D) recovering the organic or inorganic alkoxide from the catholyte compartment.

13. The process of claim 12 wherein the dividers are cation selective membranes.

14. The process of claim 12 wherein the hydroxide charged to the anolyte compartment in step (B) is an organic hydroxide.

15. The process of claim 12 wherein the hydroxide charged in step (B) is a quaternary ammonium hydroxide, a phosphonium hydroxide, or a tertiary sulfonium hydroxide.

16. A process for improving the purity of a mixture comprising water and an organic hydroxide selected from quaternary ammonium hydroxides, quaternary phosphonium hydroxides, and tertiary sulfonium hydroxides which comprises the steps of
   (A) providing an electrolysis cell which comprises an anolyte compartment containing an anode, a catholyte compartment containing a cathode and water, and at least one intermediate compartment containing water, an organic liquid, or a mixture of water and an organic liquid, said at least one intermediate compartment being separated from the anolyte and catholyte compartments by at least two dividers selected from nonionic dividers, cation selective membranes, or combinations thereof;
   (B) charging an aqueous mixture comprising water and the organic hydroxide to the anolyte compartment;
   (C) passing a current through the electrolysis cell to produce a purified mixture of water and an organic hydroxide in the catholyte compartment; and
   (D) recovering the purified aqueous mixture of the organic hydroxide from the catholyte compartment.

17. The process of claim 16 wherein the dividers are cation selective membranes.

18. The process of claim 16 wherein the hydroxide charged to the anolyte compartment in step (B) is a quaternary ammonium or quaternary phosphonium hydroxide represented by the formula

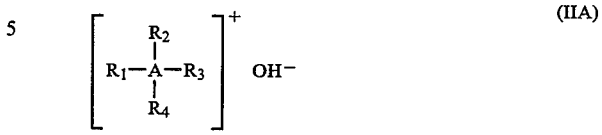

wherein A is a nitrogen or phosphorus atom, and $R_1$, $R_2$, $R_3$ and $R_4$ are each independently alkyl groups containing from 1 to about 20 carbon atoms, hydroxyalkyl or alkoxyalkyl groups containing from 2 to about 20 carbon atoms, aryl groups, or hydroxy aryl groups, or $R_1$ and $R_2$ together with A may form a heterocyclic group provided that if the heterocyclic group contains a C=A group, $R_3$ is the second bond.

19. The process of claim 18 wherein $R_1$, $R_2$, $R_3$ and $R_4$ are each independently alkyl groups containing from 1 to about 20 carbon atoms.

20. The process of claim 16 wherein the hydroxide charged to the anolyte compartment is a tertiary sulfonium hydroxide characterized by the formula

wherein $R_1$, $R_2$ and $R_3$ are each independently alkyl groups containing from 1 to about carbon atoms, hydroxy alkyl or alkoxy alkyl groups containing from 2 to about carbon atoms, aryl groups, or hydroxy aryl groups, or $R_1$ and $R_2$ together with S may form a heterocyclic group provided that if the heterocyclic group contains a C=S group, $R_3$ is the second bond.

21. The process of claim 16 wherein the hydroxide charged in step (B) is a quaternary ammonium hydroxide characterized by the formula

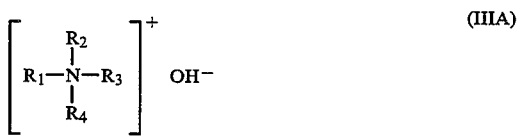

wherein $R_1$, $R_2$, $R_3$ and $R_4$ are each independently alkyl groups containing from 1 to about 10 carbon atoms, hydroxyalkyl or alkoxyalkyl groups containing from 2 to about 10 carbon atoms, aryl groups, or hydroxy aryl groups.

22. The process of claim 21 wherein $R_1$, $R_2$, $R_3$ and $R_4$ are each independently alkyl groups containing 1 to 3 carbon atoms or hydroxyalkyl groups containing 2 or 3 carbon atoms.

23. The process of claim 21 wherein $R_1$, $R_2$, $R_3$ and $R_4$ are methyl or ethyl groups.

24. A process for improving the purity of a quaternary ammonium hydroxide which comprises the steps of
   (A) providing an electrolysis cell which comprises an anolyte compartment containing an anode, a catholyte compartment containing a cathode and water, and at least one intermediate compartment containing water, said at least one intermediate compartment being separated from catholyte and anolyte compartments by at least two cation selective membranes;

(B) charging an aqueous solution comprising water and the quaternary ammonium hydroxide to the anolyte compartment;

(C) passing a current through the electrolysis cell to produce a purified organic or inorganic hydroxide in the catholyte compartment; and (D) recovering the purified aqueous quaternary ammonium hydroxide from the catholyte compartment.

25. The process of claim 24 wherein the quaternary ammonium hydroxide charged in step (B) is characterized by the formula

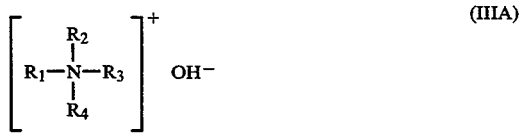 (IIIA)

wherein $R_1$, $R_2$, $R_3$ and $R_4$ are each independently alkyl groups containing from 1 to about 10 carbon atoms, hydroxyalkyl or alkoxyalkyl groups containing from 2 to about 10 carbon atoms, aryl groups, or hydroxy aryl groups.

26. The process of claim 25 wherein $R_1$, $R_2$, $R_3$ and $R_4$ are each independently alkyl groups containing 1 to 3 carbon atoms or hydroxyalkyl groups containing 2 or 3 carbon atoms.

27. The process of claim 25 wherein $R_1$, $R_2$, $R_3$ and $R_4$ are methyl or ethyl groups.

28. The process of claim 24 wherein the concentration of the quaternary ammonium hydroxide in the aqueous solution charged in step (B) is from about 3% to about 55% by weight.

29. The process of claim 24 wherein the water in the catholyte compartment and in the intermediate compartment initially contains from about 4% to about 60% by weight of the quaternary ammonium hydroxide.

30. The process of claim 24 wherein the aqueous solution containing the quaternary ammonium hydroxide charged to the anolyte compartment in step (B) is heated at an elevated temperature of from about 50° C. to about 200° C. for a period of from about 0.1 hour to about 4 days prior to being charged to the anolyte compartment.

31. A process for improving the purity of a quaternary ammonium hydroxide prepared by electrolyzing a quaternary ammonium halide salt in an electrolysis cell which comprises the steps of (A) providing an electrolysis cell which comprises an anolyte compartment containing an anode, a catholyte compartment containing a cathode and water, and an intermediate compartment containing water, said catholyte compartment being separated from the intermediate compartment by a cation selective membrane, and said anolyte compartment being separated from the intermediate compartment by a second cation selective membrane;

(B) charging an aqueous solution containing the quaternary ammonium hydroxide into the anolyte compartment, said aqueous solution containing a concentration of halide ions and a quaternary ammonium hydroxide characterized by the formula

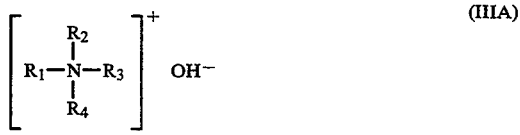 (IIIA)

wherein $R_1$, $R_2$, $R_3$ and $R_4$ are each independently alkyl groups containing from 1 to about 10 carbon atoms or hydroxy alkyl groups or alkoxy alkyl groups containing from 2 to about 10 carbon atoms;

(C) passing a direct current through the electrolysis cell for a period of time effective to form a quaternary ammonium hydroxide in the catholyte compartment; and (D) recovering an aqueous solution of the quaternary ammonium hydroxide from the catholyte compartment, said quaternary ammonium hydroxide containing less halide than the amount of halide present in the quaternary ammonium hydroxide solution charged to the anolyte compartment in step (B).

32. The process of claim 31 wherein the concentration of quaternary ammonium hydroxide in the aqueous solution recovered in step (D) is between about 5% to about 60% by weight.

33. The process of claim 31 wherein $R^1$, $R^2$, $R^3$ and $R^4$ are methyl groups.

34. The process of claim 31 wherein the quaternary ammonium hydroxide solution charged in step (B) is heated at a temperature of from about 50° C. to about 200° C. for a period of about 10 to 30 hours prior to being charged to the anolyte compartment.

35. The process of claim 31 wherein a portion of the aqueous solution recovered from the catholyte compartment in step (D) is charged to the intermediate compartment.

36. The process of claim 31 wherein a portion of the aqueous solution in the intermediate compartment is recovered and charged to the anolyte compartment.

37. The process of claim 31 wherein a portion of the aqueous solution recovered from the catholyte in step (D) is charged to the intermediate compartment and a portion of the solution in the intermediate compartment is recovered and charged to the anolyte compartment.

38. The process of claim 31 wherein a portion of the solution in the intermediate compartment is removed and replaced with water to reduce the concentration of any impurities in the solution contained in the intermediate compartment.

39. The process of claim 31 wherein the quaternary ammonium halide salt is a chloride salt.

* * * * *